United States Patent
Tomida et al.

(10) Patent No.: US 9,470,346 B2
(45) Date of Patent: Oct. 18, 2016

(54) PIPE CONNECTION JOINT

(71) Applicant: HITACHI HIGH-TECHNOLOGIES CORPORATION, Tokyo (JP)

(72) Inventors: Shoji Tomida, Tokyo (JP); Shintaro Kubo, Tokyo (JP); Mitsuhiko Ueda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/441,611

(22) PCT Filed: Nov. 20, 2013

(86) PCT No.: PCT/JP2013/081238
§ 371 (c)(1),
(2) Date: May 8, 2015

(87) PCT Pub. No.: WO2014/080925
PCT Pub. Date: May 30, 2014

(65) Prior Publication Data
US 2015/0285414 A1    Oct. 8, 2015

(30) Foreign Application Priority Data

Nov. 21, 2012 (JP) ................. 2012-254836

(51) Int. Cl.
| | |
|---|---|
| *F16L 19/00* | (2006.01) |
| *F16L 19/065* | (2006.01) |
| *G01N 30/60* | (2006.01) |

(52) U.S. Cl.
CPC ........ *F16L 19/065* (2013.01); *G01N 30/6026* (2013.01); *G01N 30/6039* (2013.01)

(58) Field of Classification Search
USPC ......... 285/245–247, 250, 353–354, 384–389
See application file for complete search history.

(56) References Cited

U.S. PATENT DOCUMENTS

| | | | | |
|---|---|---|---|---|
| 2,177,508 A | * | 10/1939 | Abbott ..................... | H05B 3/06 174/21 JS |
| 3,814,328 A | * | 6/1974 | Warning ............... | B05B 7/1254 239/296 |
| 4,669,756 A | * | 6/1987 | Cassaday ................ | F16L 47/00 285/24 |

(Continued)

FOREIGN PATENT DOCUMENTS

| | | |
|---|---|---|
| JP | 61-44087 | 3/1986 |
| JP | 2-141793 | 11/1990 |

(Continued)

OTHER PUBLICATIONS

Written Opinion of the International Searching Authority, mailed Jan. 28, 2014 in PCT/JP2013/081238.

*Primary Examiner* — Aaron Dunwoody
*Assistant Examiner* — Fannie Kee
(74) *Attorney, Agent, or Firm* — Mattingly & Malur, PC

(57) ABSTRACT

A pipe connection joint which is repeatedly usable when an analysis column is replaced with another in a liquid chromatographic device. To this end, an elastic body is built into a compression screw for inserting a pipe passed through a ferrule into the analysis column to thereby axially movably support the pipe, and a pipe clamp is secured in advance at a predetermined position of the pipe. A distance between the ferrule and the pipe clamp changes on the basis of the length of a portion of the pipe sticking out from the ferrule and the pressing force of the elastic body applied to the pipe.

6 Claims, 4 Drawing Sheets

(56) References Cited

U.S. PATENT DOCUMENTS

| | | | | |
|---|---|---|---|---|
| 5,163,722 A | * | 11/1992 | Worden | F16L 37/242 |
| | | | | 285/101 |
| 6,193,286 B1 | * | 2/2001 | Jones | G01N 30/6004 |
| | | | | 285/343 |
| 6,494,500 B1 | | 12/2002 | Todsiev | |
| 7,681,926 B2 | * | 3/2010 | Valaskovic | G02B 6/3809 |
| | | | | 285/124.5 |

FOREIGN PATENT DOCUMENTS

| | | |
|---|---|---|
| JP | 08-304370 | 11/1996 |
| JP | 2008-529003 A | 7/2008 |
| WO | 2006/083597 A2 | 8/2006 |

\* cited by examiner

PIPE CONNECTION JOINT

FIELD OF THE INVENTION

The present invention relates to a pipe connection joint to be used for a device in which a highly pressurized fluid is used such as a liquid chromatography.

BACKGROUND ART

In the liquid chromatography analysis, a mobile phase into which a sample injected by an auto-sampler is pumped into an analysis column. The sample introduced into the analysis column is separated into all components included in the sample and then each of the components is identified by a detector.

In the conventional liquid chromatography analysis, a pipe connection joint used for inserting a pipe into the analysis column consists, in general, of a ferrule and a compression screw to press the ferrule against a support face of the analysis column. When a pressure of a liquid to be pumped is as high as 40 to 60 MPa, a pressing force is applied by the compression screw to the ferrule and the ferrule is pressed against the support face so tightly that an end portion of the ferrule deforms and that there is no gap left between the ferrule and the support face. As a result, the ferrule has a function of sealing the transferred liquid and holding the pipe.

In recent years, applying a higher pressure (higher than or equal to 100 MPa) than before is required to make the analysis process completed much quicker and enable more accurate separation. There is a risk for a configuration of a ferrule and a compression screw that the ferrule cannot hold the pipe so reliably that the pipe slips through the ferrule, due to using more highly pressurized liquid.

SUMMARY OF THE INVENTION

A patent document 1 discloses a structure in which the pipe is forcibly held by mechanical means of both the ferrule and a pipe clamp additionally installed.

PRIOR ART DOCUMENT

Patent Document

Patent Document 1: JP2008-529003A

SUMMARY OF THE INVENTION

Objective to be Achieved by the Invention

A shape of a pipe joint portion of the analysis column is determined in principle based on a flow passage of the mobile phase liquid, the support face in a conical shape against which the ferrule is pressed and a shape of the compression screw of a female type. Some analysis columns have the pipe joint portion in a shape which is so different from those of other analysis columns that for example, a depth of a pipe insertion portion of these analysis columns into which the pipe is inserted are very different from those of the other analysis columns. Therefore, when an operator connects the pipe with the analysis column, the operator inserts the pipe into the pipe insertion portion and screws so tight the compression screw as to reduce a dead volume while keeping the pipe pressed against a bottom face of the pipe insertion portion. Accordingly it is necessary to use both hands to perform this connection operation, which is a problem with low operation efficiency. In addition, there is a risk for low analysis accuracy due to the dead volume caused by a variation in the pressing force to be applied to the ferrule among operators.

Especially, when a new analysis method is developed, a plurality of analysis columns are so often replaced with one another that a pipe connection joint has to be used repeatedly for plural times.

However, since the pipe is held by a friction force in the method as described in Patent Document 1, a high pressure has to be applied in the radius direction of the pipe, which could result in the pipe clamp biting onto the pipe and the pipe being scratched. As a result, it is difficult to use one pipe connection joint for plural times because it cannot hold a pipe sufficiently tight.

An objective of the present invention is to provide a pipe connection joint that is used for the super high speed liquid chromatography device using high pressure liquid and enables improvement of analysis accuracy and a pipe connection joint being used repeatedly for plural times when the analysis column is changed to another one.

A pipe connection joint of an embodiment to achieve the objective mentioned above comprises a ferrule having a inner hole into which a pipe is inserted and one end portion in a wedge shape, a compression screw that has a first inner hole having a first diameter (x1) into which the pipe is inserted and a second inner hole having a second diameter (x2) being different from the first diameter (x1) and has one end portion in which a recess portion is formed to receive the other end portion of the ferrule, a first elastic body support that is fixed in advance to the pipe and disposed in the second inner hole, an elastic body that is disposed in the second inner hole and supports the elastic body in such a way that the pipe is movable, a second elastic body support that has an inner hole into which the pipe is inserted, is fixed to the compression screw and has an end portion to support the elastic body disposed in the compression screw, a pipe clamp fixed in advance to such a position of the pipe that the elastic body and the second elastic body support are positioned between the first elastic body support and the pipe clamp, and a pipe clamp holder that has an inner hole into which the pipe is inserted and supports an end portion of the pipe clamp.

The above embodiment enables improvement of analysis accuracy and an pipe connection joint being repeatedly used when an analysis column is replaced.

DETAILED DESCRIPTION OF THE EMBODIMENT FOR PRACTICING THE INVENTION

Hereinafter are explained embodiments of the present invention in detail.

Figure 1:
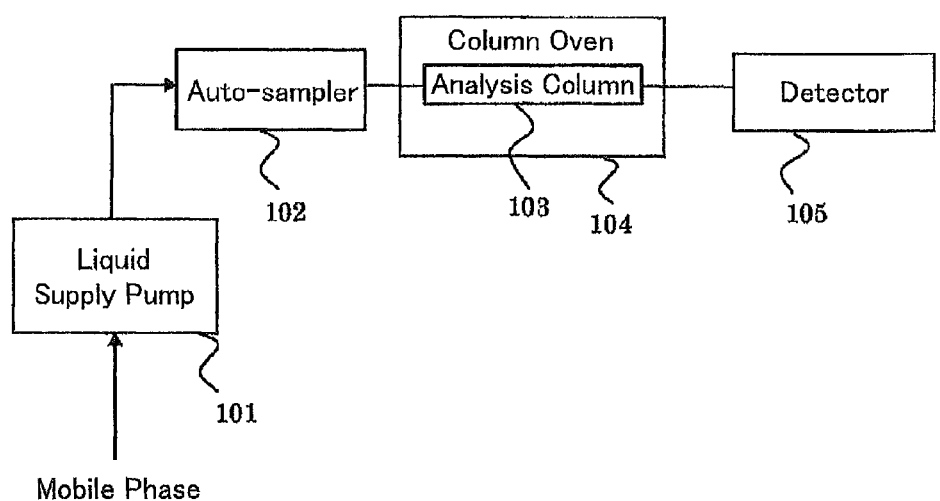
FIG. 1 shows a basic configuration of the liquid chromatography device.

FIG. 1 shows a basic configuration of the liquid chromatography device. This device comprises a liquid supply pump 101, an auto-sampler 102 for injecting a sample, an analysis column 103, a column oven 104 to keep the analysis column at a predetermined constant temperature and a detector 105.

The pipe connection joint to be explained in this specification is used for connecting the analysis column above mentioned with other part.

Example 1

Figure 2:
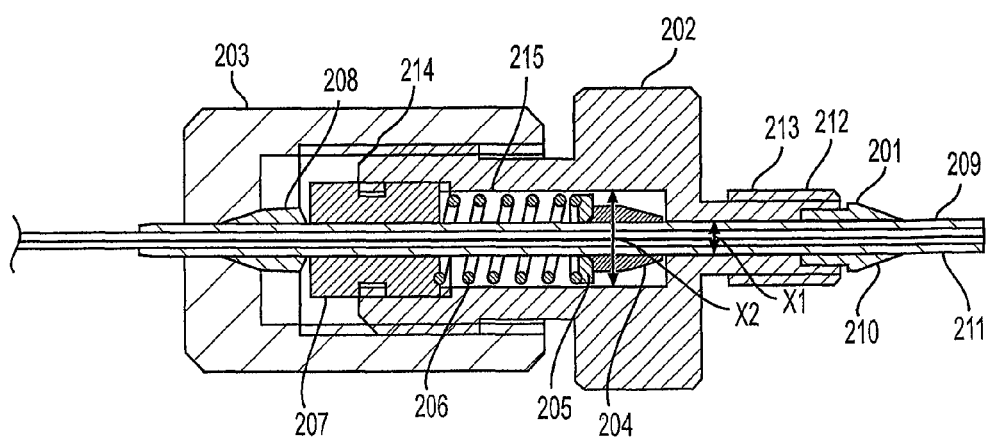
FIG. 2 shows a cross section of a structure of a pipe connection joint of an embodiment of the present invention.

FIG. 2 shows a cross section of a structure of a pipe connection joint of an embodiment of the present invention. The ferrule 201 that is intended to seal the liquid has a ferrule forefront portion 210 having a cross section in a wedge shape and an inner hole into which a pipe 209 is inserted. A compression screw 202 has a ferrule receiving portion 212 that is formed to receive the ferrule 201 and a first male screw 213 to fix the ferrule 201.

The compression screw 202 has an inner hole having a first diameter (x1) into which the pipe 209 is inserted and a hollow structure 215 in which there is formed an inner hole having an second diameter (x2) that is larger than the first diameter (x1). In the inner hole with the second diameter (x2) are arranged the pipe 209, an elastic body stopper 204 that is fixed in advance at a predetermined position of the pipe 209, an elastic body stopper ring 205 and an elastic body stopper 207. The elastic body stopper 207 is fixed to the compression screw 202. Thus, the elastic body stopper 207 is attached to the compression screw 202 and the pipe 209 is supported by the elastic body 206 and able to move in its axis direction.

A pipe clamp 208 fixed in advance to the pipe 209 is disposed at a position that is spaced apart from the ferrule 201 and a pipe clamp holder 203 to mechanically hold the pipe clamp 208 is configured to be in mesh with and locked by the second male screw 214. When the pipe clamp holder 203 is screwed tight on the compression screw 202, a structure in which the pipe clamp 208 holds the pipe 209 is made.

Since the pipe 209 is configured to be movable in its axis direction according to the embodiment above explained, the pipe connection joint can be attached to various types of the analysis columns which have different pipe insertion depths by attaching the compression screw 202. It is not necessary to screw the compression screw 202 while pressing the pipe 209, which, in contrast, is needed for the conventional pipe connection.

In addition, this embodiment enables improvement of the analysis accuracy, because the variation in the dead volume is reduced.

Moreover, since the pipe clamp 208 fixed in advance to the pipe 209 at a position spaced apart from the ferrule 201 and the pipe clamp holder 203 is attached to the compression screw 202, a pipe connection joint having a higher withstand pressure is realized.

Furthermore, since this embodiment makes use of a structure in which the pipe clamp 208 is fixed at a predetermined position of the pipe 209 and the pipe clamp holder 203 held on the compression screw 202 is changed to a position that is appropriate for the pipe insertion depth of the analysis column, there is no risk of damaging the pipe 209 and lowering the pipe holding force for various pipe insertion depths of the analysis columns.

Accordingly, the pipe connection joint of the present embodiment can be used for plural times. In an embodiment above mentioned, although the elastic body stopper 207 is made to be screwed into and fixed by the compression screw 202, the elastic body stopper 207 may be fixed by other fixing methods such as press fitting or crimping. In addition the present embodiment includes the elastic body stopper ring 205, it is possible to omit this elastic body stopper ring 205 if the elastic body stopper 204 is made so large that the elastic body stopper 204 is able to sufficiently support the elastic body 206 on its own.

Example 2

Figure 3A:
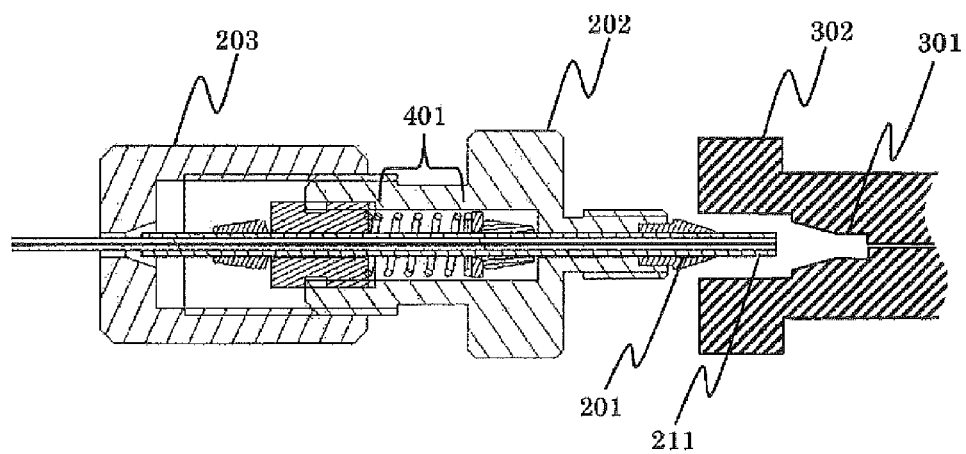
FIG. 3A shows a first connection condition of the pipe connection joint and an analysis column.
Figure 3B:
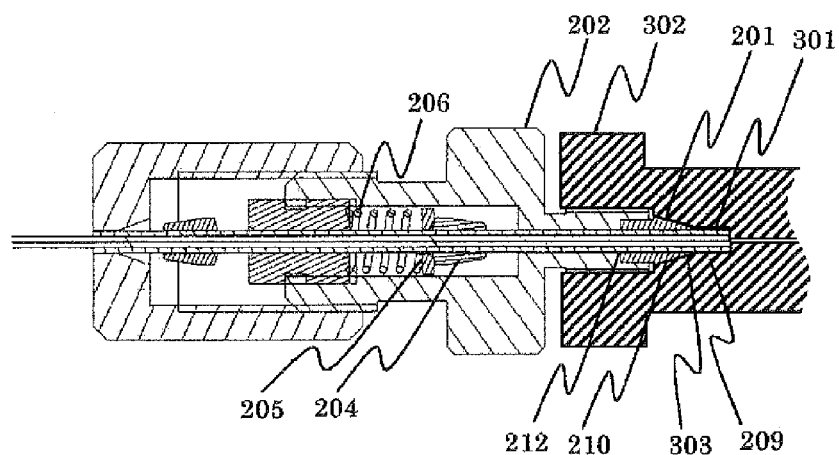
FIG. 3B shows a second connection condition of the pipe connection joint and the analysis column.
Figure 3C:
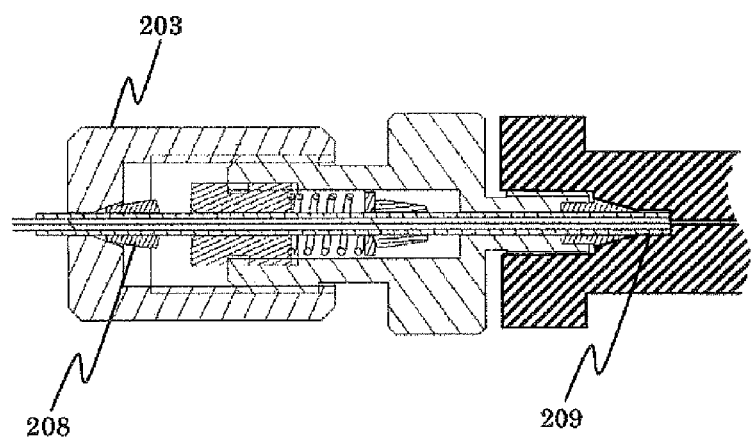
FIG. 3C shows a third connection condition of the pipe connection joint and the analysis column.

FIG. 3A, FIG. 3B and FIG. 3C show an example of the pipe connection sequence with the pipe connection joint structure as shown in FIG. 2. Hereinafter the pipe connection sequence is explained with reference to the figures.

Before the pipe 209 is connected, the pipe clamp holder 203 is loosened to get back to a position where the pipe clamp holder 203 is spaced a sufficiently long distance apart from the ferrule 201 relative to a sticking out portion 211 of the pipe 209 from the ferrule 201, as shown in FIG. 3A. With the pipe clamp holder disposed at this position, the sticking out portion 211 can be put into a pipe insertion portion 301 of each of various kinds of analysis columns. Next, the compression screw 202 with the pipe connection joint being what is shown in FIG. 3A is attached to the analysis column 302. The pipe connection joint after attachment is shown in FIG. 3B.

As the compression screw 202 is being screwed to come toward and get engaged with the analysis column 302, an end face of the pipe 209 comes in contact with the bottom face of the pipe insertion portion 301 of the analysis column 302. Then, the compression screw 202 is further screwed to move toward the analysis column 302, the pipe 209 moves in an opposite direction to a direction of the analysis column in its direction. The elastic body stopper 204 that is fixed to the pipe 209 and the elastic body stopper ring 205 move in the same direction as the pipe 209 deforms the elastic body 206.

A counter force of the elastic body caused by deformation of the elastic body 206 is a force to press the end face of the pipe 209 against the bottom face of the pipe insertion portion 301 and a dead volume between the analysis column 302 and the pipe insertion portion 301 is reduced. As the compression screw 202 is further screwed up by turning the compression screw 202, the ferrule forefront portion 210 that is in a wedge shape and formed on the ferrule 201 comes in contact with the ferrule forefront support portion 303.

Then the compression screw 202 is further screwed up, a force is applied to the ferrule receiving portion 212. As a result, there is a pressure applied among the ferrule 201, the pipe 209, the ferrule forefront portion 210 and the ferrule forefront support portion 303 due to properties of the ferrule forefront portion 210 and a liquid seal face is formed. Subsequently, a pipe clamp holder 203 that was loosened is screwed up and is pressed against the clamp holder 208 that was fixed in advance to the pipe 209, which results in an increased pipe holding force. This state is shown in FIG. 3C.

As explained, although there is a variation in the pipe insertion portion 301, a pipe connection joint can be used for plural times with a structure in which the pipe clamp 208 that was fixed in advance to the pipe 209 is held on the pipe clamp holder 203 by the support force applied by the elastic body 206 to the pipe 209 which is dependent on the sticking out portion 211 of the pipe 209 from the ferrule 201 and a elastic body deformation amount 401 of the elastic body 206.

Example 3

Figure 4A:
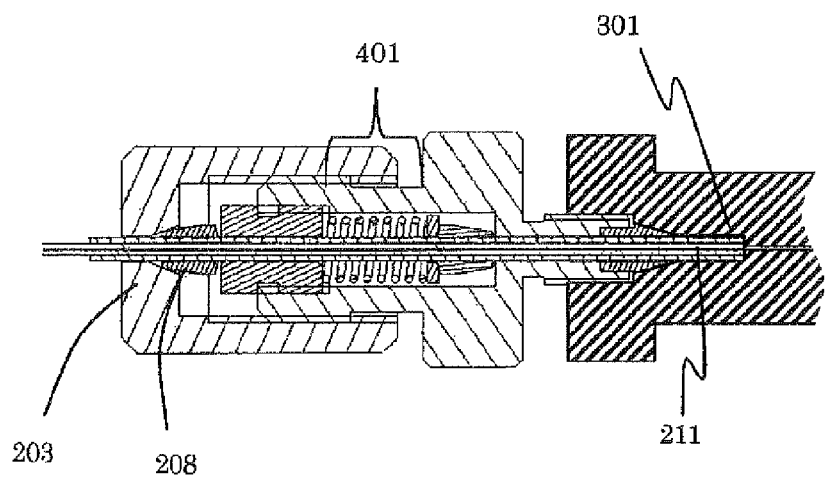
FIG. 4A shows a first relation between a length of a sticking out portion of a pipe and a deformation amount of an elastic body.
Figure 4B:
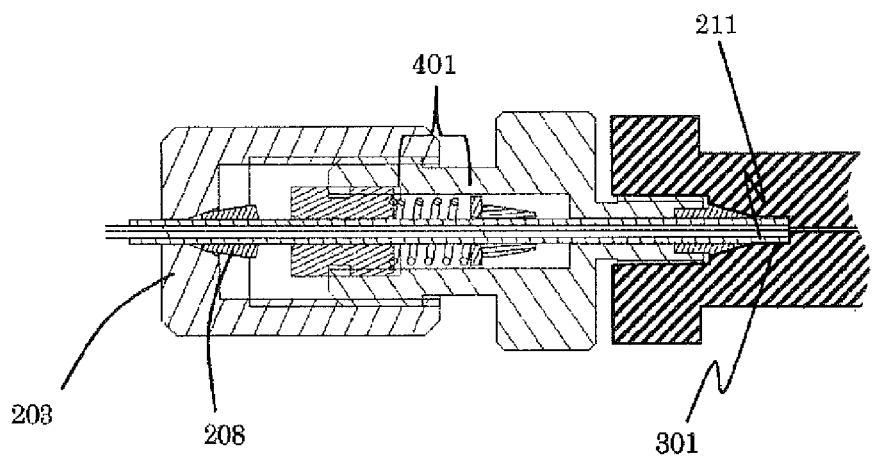
FIG. 4B shows a second relation between a length of a sticking out portion of a pipe and a deformation amount of an elastic body.

FIGS. 4A, 4B show relations between a length of a sticking out portion of a pipe and a deformation amount of an elastic body FIG. 4A shows a connection state between the pipe and the column when the length of a sticking out portion 211 of the pipe is long while FIG. 4B shows a connection state between the pipe and the column when the sticking out portion 211 of the pipe is short. As shown in FIGS. 4A, 4B, the elastic body deformation amount 401 of the elastic body is dependent on the length of the sticking out portion 211. To be specific, the shorter the sticking out portion 211 from the ferrule forefront portion 210 with the pipe 209 inserted into the pipe insertion portion 301 of the analysis column 302, the larger the elastic body deformation amount 401 is and the longer a distance between the ferrule 201 and the pipe clamp 208 is. A pressing force applied to a bottom face of the pipe insertion portion 301 is so high as to reduce the dead volume. Thus, the distance by which the ferrule 201 and the pipe clamp 208 are spaced apart from each other is determined based on the sticking out portion 211 and the pressing force determined by the elastic body deformation amount 401.

If a pipe connection joint as has been described above is applied to a liquid chromatography device inclusive of the liquid supply pump 101, an injection device, the analysis column 103, the detector 105 and a data processing device, replacing an analysis column 103 with another is easier. Moreover analysis accuracy is improved and it is possible to use the pipe connection joint for plural times. In addition, a turnaround time for developing a analysis method can be shortened.

Example 4

Figure 5:
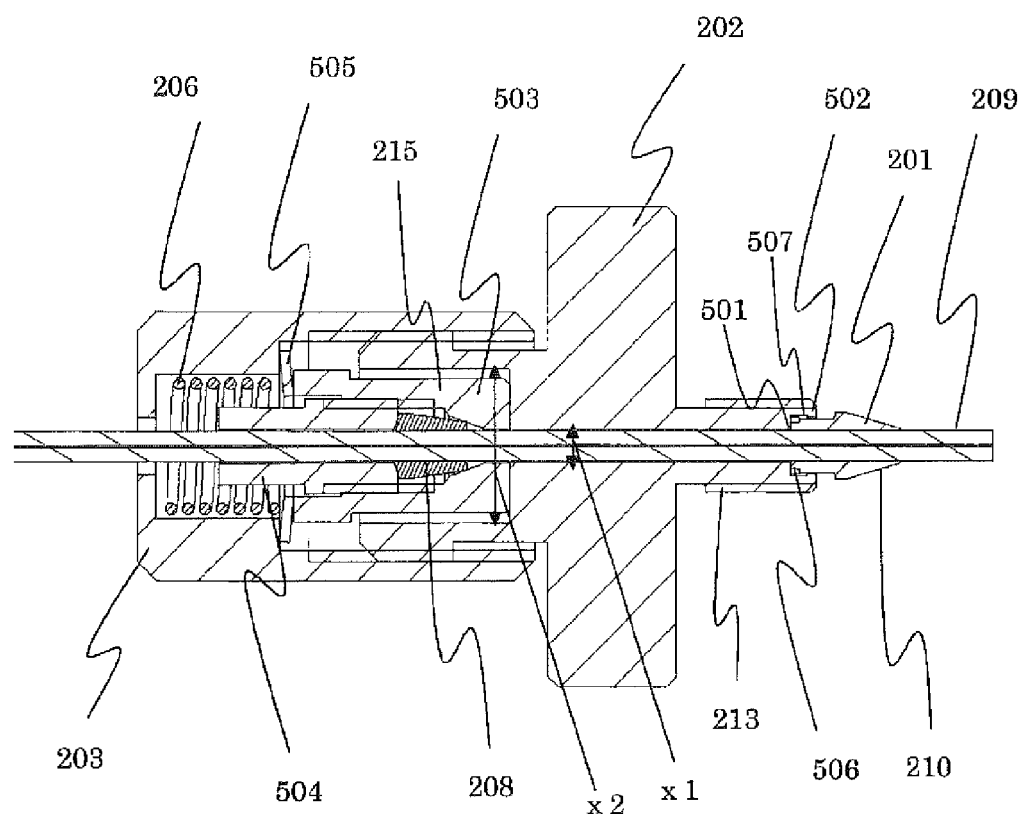
FIG. 5 shows a cross section of one of other examples of the pipe connection joint.

FIG. 5 shows a cross section of other examples of the pipe connection joint. A ferrule 201 for sealing the liquid comprises the ferrule forefront portion 210 formed to have a cross section in a wedge shape and an opposite end portion 501 on which a reversely threaded male screw 506 is formed and has an inner hole into which the pipe 209 is inserted. The compression screw 202 comprises a ferrule receiving portion 502 to receive the ferrule 201. In the ferrule receiving portion 502, a reversely threaded female thread 507 is formed so as to be in mesh with the reversely threaded male screw 506 formed on the opposite end portion 501 of the ferrule 201.

With the above mentioned structure applied, the ferrule 201 is prevented from coming off by the reversely threaded male screw on the ferrule 201 being in mesh with the reversely threaded female screw 507 in the compression screw 202.

In addition, the compression screw 202 has a hollow structure 215 consisting of an inner hole having a first diameter of x1 into which the pipe 209 is inserted and another hole having a second diameter of x2 that is larger than x1. In the inner hole of the second diameter of x2 are arranged the pipe 209, the pipe clamp 208 fixed in advance at a predetermined position of the pipe 209, a coned disc elastic body support 503 and a pipe clamp support member 504. The pipe clamp 208 is constantly kept pressed between the coned disc elastic body support 503 and the pipe clamp support member 504, which results in holding the pipe 209 more tight.

When the pipe clamp holder 203 is loosely attached to the compression screw 202, a force generated by the elastic body 206 on the coned disc elastic body support 503 is predominant and the position of the coned disc elastic body support 503 is movable in the axial direction of the pipe 209.

In addition, when the clamp holder 203 is screwed tight on the compression screw 202, the coned disc elastic body 505 is deformed by a force applied by the pipe clamp holder 203 and the coned disc elastic body support 503 is pressed.

When this structure is used, the decrease in the pressing force caused by the temperature variation and the like during measurement is reduced.

The present invention should not be limited to the above embodiment and may be applied to any structure with which the function indicated by the claims or the above mentioned embodiment is achieved.

EXPLANATION OF SIGNS

101 Liquid Supply Pump
102 Auto-sampler
103 Analysis Column
104 Column Oven
105 Detector
201 Ferrule
202 Compression Screw
203 Pipe Clamp Holder
204 Elastic Body Stopper (First Elastic Body Stopper)
205 Elastic Body Stopper Ring
206 Elastic Body
207 Elastic Body Stopper (Second Elastic Body Stopper)
208 Pipe Clamp
209 Pipe
210 Ferrule Forefront Portion
211 Sticking Out Portion
212 Ferrule Receiving Portion
213 First Male Screw
214 Second Male Screw
215 Hollow Structure
301 Pipe Insertion Portion
302 Analysis Column
303 Ferrule Forefront Support Portion
401 Elastic body deformation amount
501 Ferrule Opposite End Portion
502 Compression Screw Forefront Portion
503 Coned Disc Elastic Body Support
504 Pipe Clamp Support Member
505 Coned Disc Elastic Body
506 Reversely Threaded Male Screw
507 Reversely Threaded Female Screw
x1 First Diameter
x2 Second Diameter

What is claimed is:
1. A pipe connection joint for connecting a pipe with an analysis column of a liquid chromatography device comprising:

a ferrule having an inner hole into which a pipe is inserted and an end portion having a wedge shape;

a compression screw having a first inner hole with a first diameter into which the pipe is inserted and a second inner hole with a second diameter being different from the first diameter, and one end of the compression screw has a recessed portion;

an elastic body disposed in the second inner hole supporting the pipe in such a way that the pipe is movable;

a first elastic body support that is fixed to the pipe and disposed in the second inner hole;

a second elastic body support fixed to the compression screw and having an inner hole into which the pipe is inserted, and having an end portion supporting the elastic body disposed in the compression screw;

a pipe clamp holder that supports an end portion of a pipe clamp, and has an inner hole into which the pipe is inserted, the pipe clamp holder being mechanically engaged with the compression screw, and wherein the pipe clamp is disposed in the pipe clamp holder and is fixed to the pipe, wherein the elastic body and the second elastic body support are positioned between the first elastic body support and the pipe clamp in an axial direction of the pipe, wherein the wedge-shaped end portion of the ferrule extends from the compression screw, wherein the second elastic body support is disposed in the inner hole of the pipe clamp holder, and wherein the other end portion of the ferrule is disposed within the recessed portion of the compression screw.

2. The pipe connection joint as described in claim 1, wherein a distance between the ferrule and the pipe clamp with the pipe being engaged with the column is relative to a length of the pipe extending from the wedge-shaped end portion of the ferrule.

3. The pipe connection joint as described in claim 2, wherein the longer the length of the pipe extending from the wedge-shaped end portion of the ferrule, the shorter a distance between the ferrule and the pipe clamp is.

4. The pipe connection joint as described in claim 1, wherein the compression screw is fixed to the second elastic body support by screwing.

5. The pipe connection joint as described in claim 1, wherein the inner hole of the pipe clamp holder has a third diameter greater than the second diameter of the second inner hole of the compression screw.

6. The pipe connection joint as described in claim 1, wherein only the pipe is disposed in the first inner hole of the compression screw.

* * * * *